US006428810B1

(12) United States Patent
Bergstrand et al.

(10) Patent No.: US 6,428,810 B1
(45) Date of Patent: Aug. 6, 2002

(54) PHARMACEUTICAL FORMULATION COMPRISING OMEPRAZOLE

(75) Inventors: Pontus Bergstrand, Gothenburg; Peter Wang, Mölndal, both of (SE)

(73) Assignee: AstraZeneca AB, Sodertalje (SE)

(*) Notice: Subject to any disclaimer, the term of this patent is extended or adjusted under 35 U.S.C. 154(b) by 0 days.

(21) Appl. No.: 09/485,218

(22) PCT Filed: Nov. 3, 1999

(86) PCT No.: PCT/SE99/01989

§ 371 (c)(1),
(2), (4) Date: Feb. 4, 2000

(87) PCT Pub. No.: WO00/27366

PCT Pub. Date: May 18, 2000

(30) Foreign Application Priority Data

Nov. 5, 1998 (SE) .............................................. 9803772

(51) Int. Cl.[7] .............................. A61K 9/36; A61K 9/20
(52) U.S. Cl. ........................ 424/480; 424/464; 424/468; 424/472; 424/474
(58) Field of Search ................................ 424/464, 465, 424/467, 468, 469, 470, 480, 489; 514/960, 965

(56) References Cited

U.S. PATENT DOCUMENTS

| | | | |
|---|---|---|---|
| 5,690,960 A | * 11/1997 | Bengtsson et al. | 424/480 |
| 5,817,338 A | * 10/1998 | Bergstrand et al. | 424/468 |
| 6,090,827 A | 7/2000 | Erickson et al. | 514/338 |

FOREIGN PATENT DOCUMENTS

| | | |
|---|---|---|
| EP | 0005129 | 10/1979 |
| EP | 0124495 | 11/1984 |
| EP | 0247983 | 12/1987 |
| EP | 0496437 | 7/1992 |
| WO | 9427988 | 12/1994 |
| WO | 9501977 | 1/1995 |
| WO | 9601623 | 1/1996 |
| WO | 9725066 | 7/1997 |

OTHER PUBLICATIONS

Pilbrant, A. et al., "Development of an oral formulation of omeprazole", *Scand. J. Gastroenterol*, 1985; 20 (suppl): 113–120.

* cited by examiner

Primary Examiner—Thurman K. Page
Assistant Examiner—Charesse L. Evans
(74) Attorney, Agent, or Firm—White & Case LLP

(57) ABSTRACT

An enteric coated oral pharmaceutical formulation comprising as active ingredient a compound selected from the group of omeprazole, an alkaline salt of omeprazole, one of the single enantiomers of omeprazole and an alkaline salt of one of the single enantiomers of omeprazole, wherein the formulation comprises a core material that comprises the active ingredient and optionally an alkaline reacting compound, the active ingredient is in admixture with a pharmaceutically acceptable excipient, such as for instance a binding agent, and on said core material a separating layer and an enteric coating layer. A hydroxypropyl cellulose (HPC) with a specific cloud point is used in the manufacture of the claimed pharmaceutical formulations. Furthermore, the application describes the processes for their preparation and the use of the claimed formulations in medicine.

22 Claims, 4 Drawing Sheets

Cloud point determinations of the two different qualities of HPC named Type A and Type B (according to Example 3).

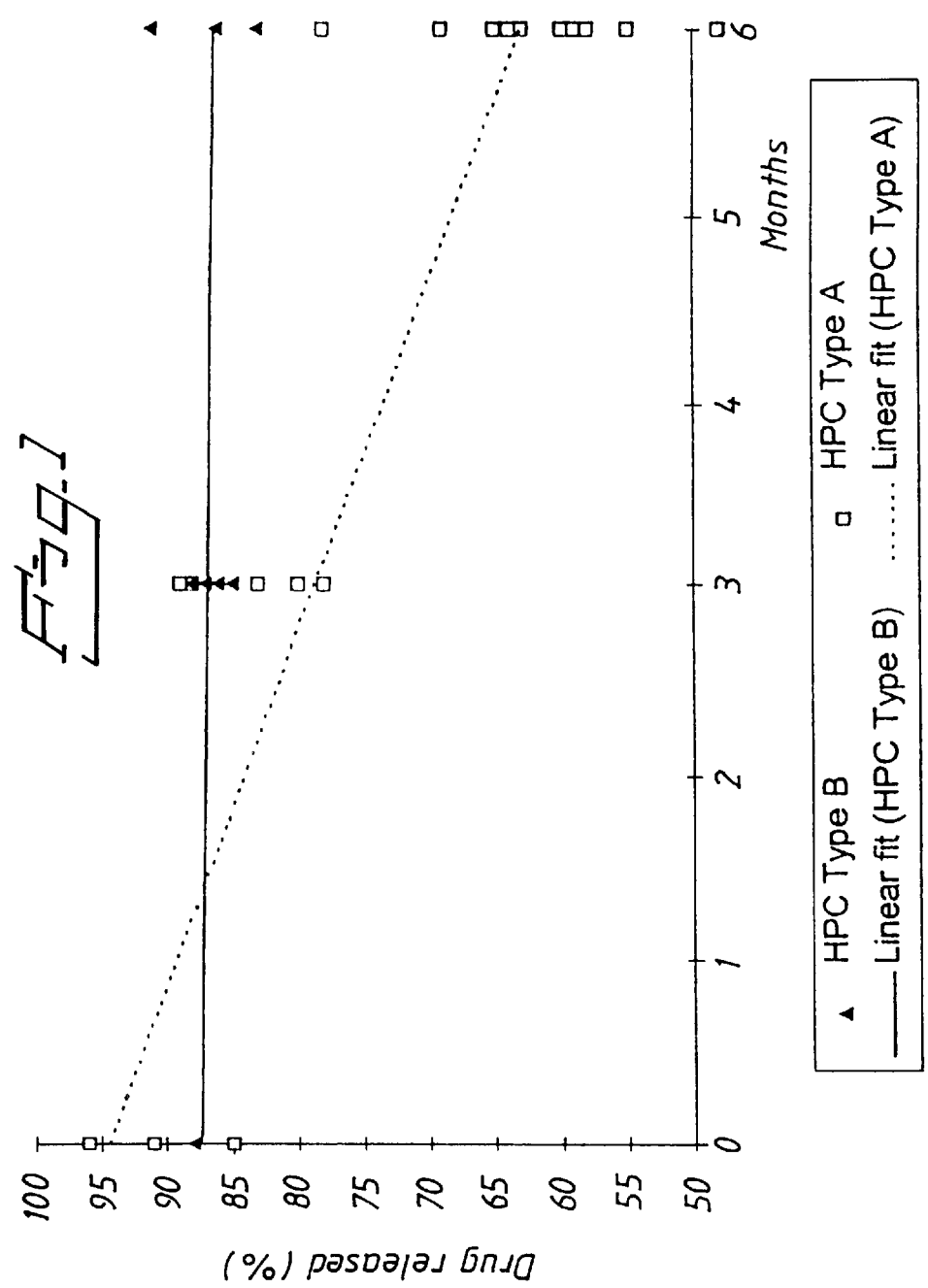
Figure 1. Drug released, after pre-exposure 2 hours to 0.1 M HCl and 30 minutes in buffer pH 6.8, from tablets containing HPC Type A and HPC Type B in the separating layer of enteric coated pellets (according to Example 2).

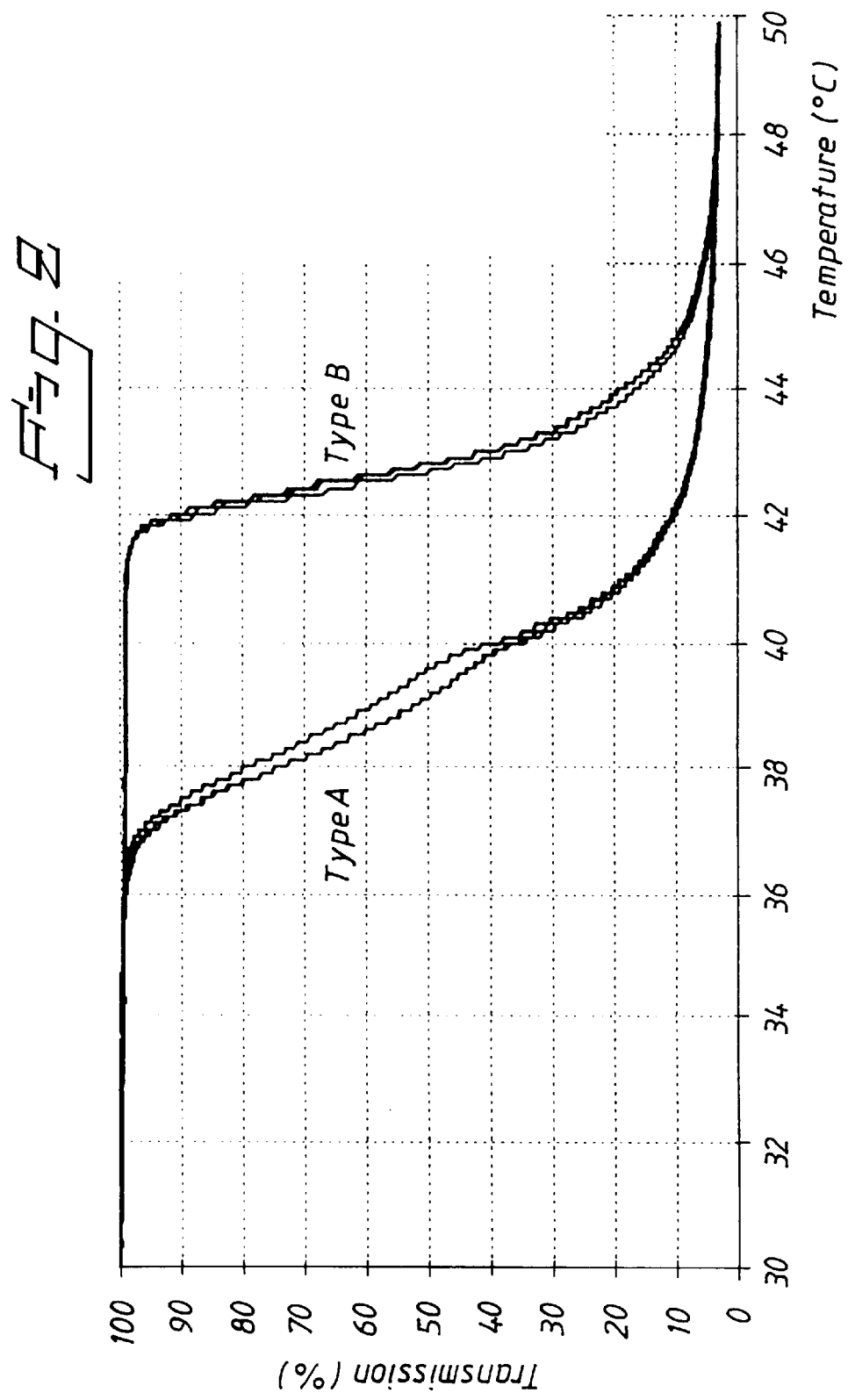
Figure 2. Cloud point determinations of the two different qualities of HPC named Type A and Type B (according to Example 3).

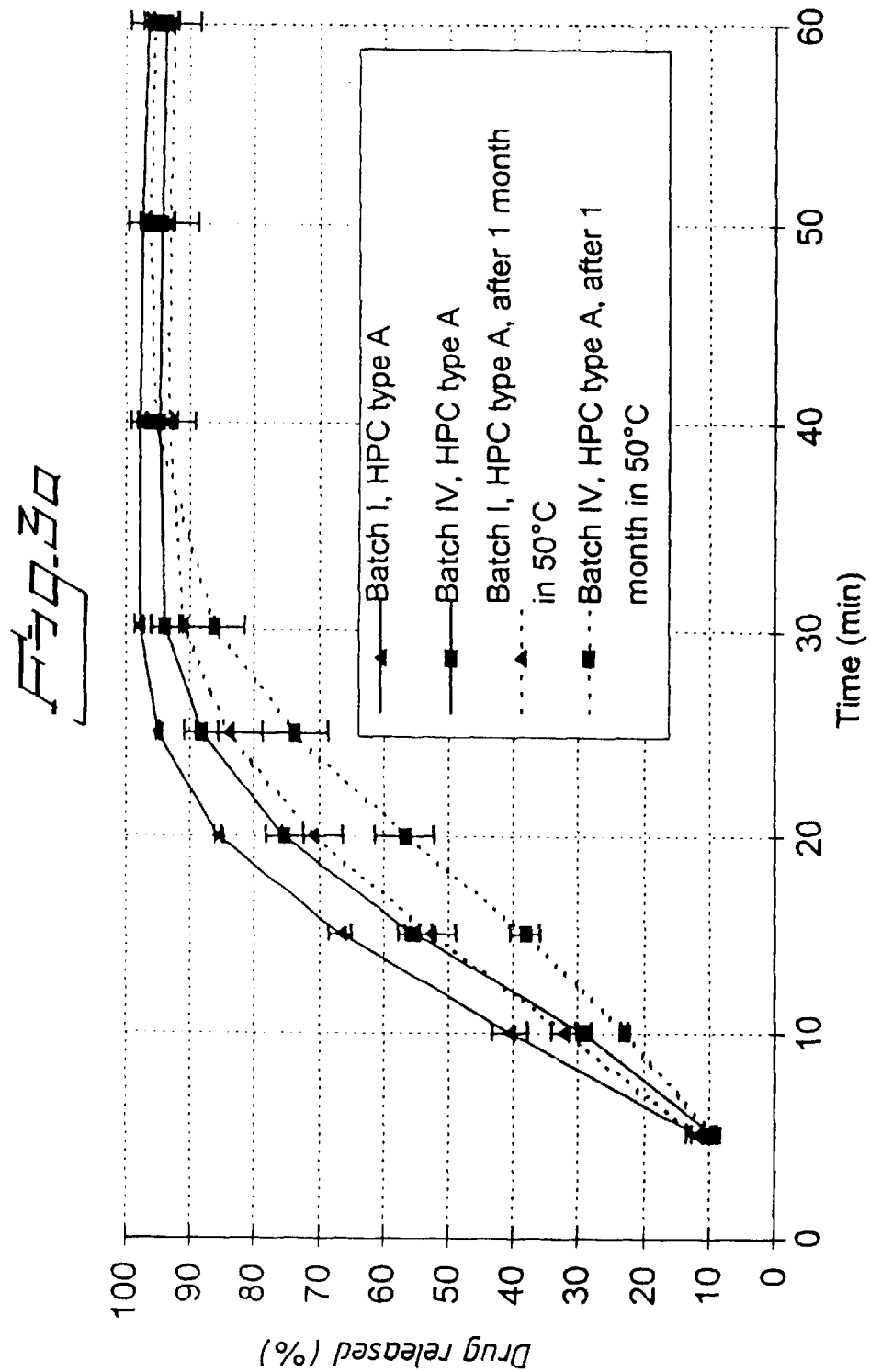
Figure 3a). Release of omeprazole from formulations containing HPC type A (according to Example 1) in separating layer of enteric coated pellets, before and after storage.

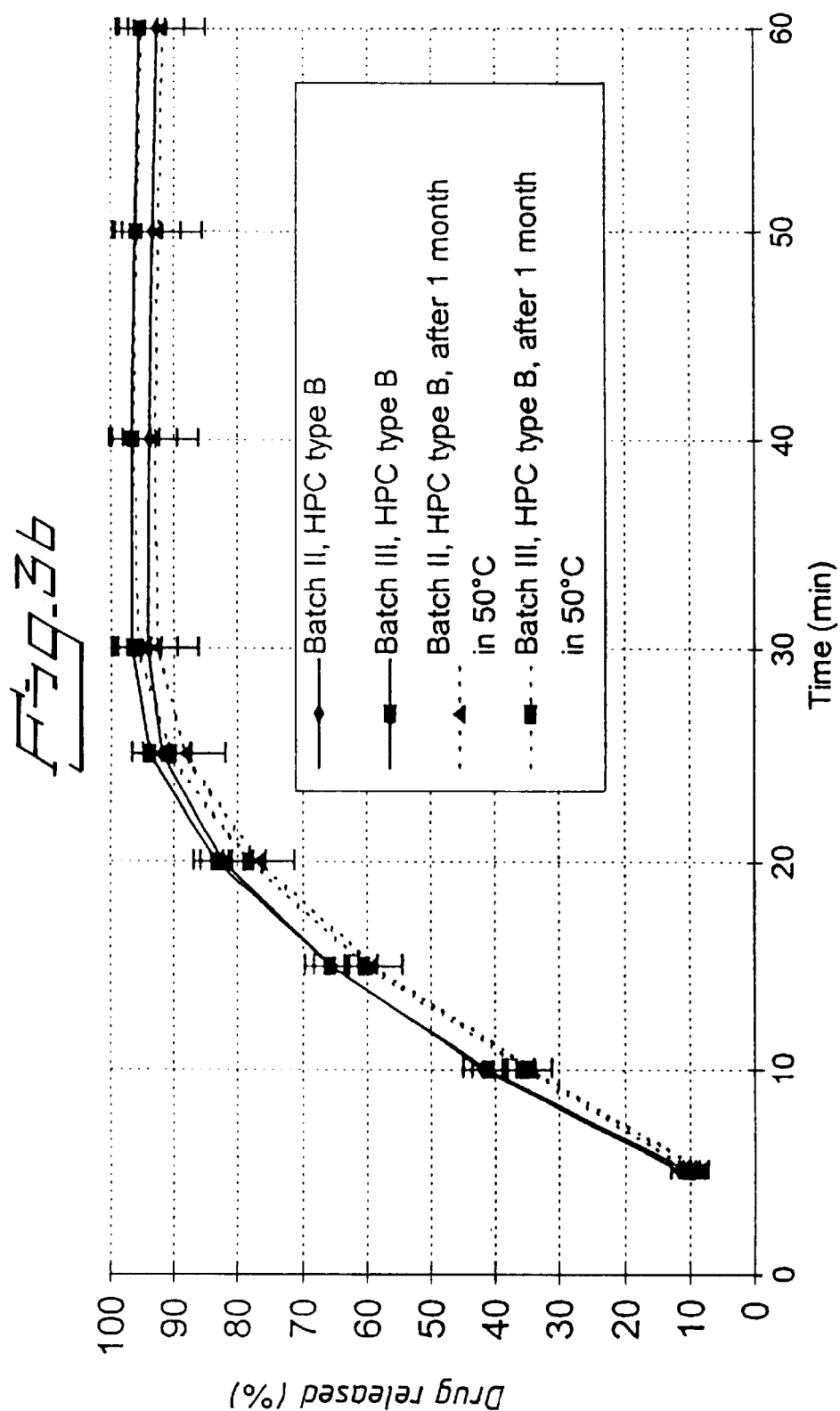
Figure 3b). Release of omeprazole from formulations containing HPC type B (according to Example 1) in separating layer of enteric coated pellets, before and after storage.

PHARMACEUTICAL FORMULATION COMPRISING OMEPRAZOLE

FIELD OF THE INVENTION

The present invention relates to an oral pharmaceutical formulation comprising the acid labile $H^+$, $K^+$-ATPase inhibitor omeprazole, an alkaline salt of omeprazole, one of the single enantiomers thereof or an alkaline salt of one of the single enantiomers of omeprazole. In the following these compounds are referred to as omeprazole. The formulation is in the form of a multiple unit dosage form that comprises enteric coating layered units of omeprazole. More specifically, the units comprise a core material that comprises omeprazole optionally in admixture with an alkaline reacting substance, and in admixture with one or more pharmaceutically acceptable excipients such as a binding agent, a filling agent and/or a disintegrating agent. Furthermore, each unit comprises a separating layer to separate the enteric coating layer from the core material. The separating layer comprises a specific quality of hydroxypropyl cellulose (HPC), and optionally pharmaceutical excipients. More specifically, the HPC quality is defined by having a specific cloud point.

Furthermore, the present invention refers to the use of the specific quality of HPC in the manufacture of a pharmaceutical formulation comprising omeprazole, and the use of such a pharmaceutical formulation in medicine.

BACKGROUND OF THE INVENTION

Omeprazole, an alkaline salt thereof, the single enantiomers of omeprazole and an alkaline salt of the single enantiomers of omeprazole, all compounds hereinafter referred to as omeprazole, are used in the treatment of gastric acid related diseases. Omeprazole and pharmaceutically acceptable salts thereof are described in EP 5129, and some specific alkaline salts of omeprazole are described in EP 124 495 and WO95/01977. Certain salts of the single enantiomers of omeprazole and their preparations are described in WO94/27988.

Omeprazole is generally known to be useful for inhibiting gastric acid secretion in mammals and man by controlling gastric acid secretion at the final step of the acid secretory pathway. Thus, in a more general sense, it may be used for prevention and treatment of gastric-acid related diseases in mammals and man, including e.g. reflux oesophagitis, gastritis, duodenitis, gastric ulcers and duodenal ulcers. Furthermore, it may be used for treatment of other gastrointestinal disorders where gastric acid inhibitory effect is desirable e.g. in patients on NSAID therapy, in patients with non ulcer dyspepsia, in patients with symptomatic gastro-oesophageal reflux disease, and in patients with gastrinomas. It may also be used in a patient in intensive care situations, in a patient with acute upper gastrointestinal bleeding, pre-and post-operatively to prevent aspiration of gastric acid and to prevent and treat stress ulceration. Further, it may be useful in the treatment of psoriasis as well as in the treatment of Helicobacter infections and diseases related to these, as well as in the treatment or prophylaxis of inflammatory conditions in mammals, including man.

Omeprazole is, however, susceptible to degradation or transformation in acidic and neutral media. The degradation is catalyzed by acidic compounds and is stabilized in mixtures with alkaline compounds. The chemical stability of omeprazole is also affected by moisture, heat, and organic solvents and to some degree by light.

Due to the chemical stability properties of omeprazole, it is obvious that an oral solid dosage form comprising omeprazole must be protected from contact with the acidic gastric juice. Omeprazole must also be transferred in intact form to that part of the gastrointestinal tract where pH is near neutral and where rapid absorption can occur.

A pharmaceutical oral dosage form of omeprazole is best protected from contact with acidic gastric juice by an enteric coating layer. For instance, EP 247 983 describes enteric coated formulations of omeprazole. Such as formulation contains omeprazole in the form of a core unit containing omeprazole together with an alkaline salt or containing an alkaline salt of omeprazole optionally together with an alkaline salt, the core unit is layered with a separating layer and an enteric coating layer. In WO 96/01623 a multiple unit tableted dosage formulation comprising omeprazole is described.

The oral formulations described in EP 247 983 and the tablet formulations described in WO 96/01623 are examples of enteric coating layered formulations that comprise or optionally comprise a separating layer to separate the acidic enteric coating material from omeprazole being an acid susceptible substance. HPC may be used in a layer that separates the core material from the enteric coating layer in the described formulations. All ingredients, including HPC qualities, used in a pharmaceutical preparation must fulfil strict criteria, such as for instance requirements defined in pharmacopoeial monographs.

The rate of release of omeprazole from a pharmaceutical dosage form can influence the total extent of absorption of omeprazole into the general circulation (Pilbrant and Cederberg, Scand. J. Gastroenterology 1985; 20 (suppl. 108) p. 113–120). Therefore the limits for rate of release of the omeprazole from the pharmaceutical formulation are stated in the marketing approval for the products. The release of omeprazole is affected both by the chemical stability of the active substance and the release stability of the pharmaceutical formulation. If the formulation is unstable with respect to the release rate, the drug will have a non-accepted storage time, i.e. the expiration period for the product will be too short.

It has now surprisingly been found that different batches of HPC, which fulfil all pharmacopoeial requirements, used as material for the separating layer in a pharmaceutical formulation comprising omeprazole, may result in different release rate over time. Thus, the storage period for the pharmaceutical formulation may not be acceptable. One parameter of interest for the HPC's influence on the release stability is its water solubility.

The aqueous solubility of HPC decreases with increasing temperature due to polymer phase separation. This is observed as a clouding of the polymer solution when the temperature is increased. Cloud point is the temperature at which this polymer phase separation occurs. Cloud point is determined by measuring the light transmission through the polymer solution. The light transmission of a specific system where the polymer is dissolved, that is a transparent polymer solution without clouding, is defined as light transmission 100%. In this patent application cloud point is defined as the temperature where the light transmission of a specific system is 96% when a commercial instrument from Mettler is used. For other cloud point systems and instruments another light transmisson may be specified for each system.

One problem that can be avoided by the new formulation and use of a specific quality of HPC, is that the storage period for the dosage form can be extended and guaranteed. From an economical aspect it is advantageous to specify and check the HPC quality thereby keeping a long expire date of the dosage form.

OUTLINE OF THE INVENTION

It has now been found that a quality of HPC with a cloud point of not less than 38° C. determined as the temperature where the light transmission of a specified system is 96% measured by a Mettler FP90/FP 81C instrument is desirable in an enteric coating layered pharmaceutical formulation comprising omeprazole. Preferably, the HPC should have a cloud point of not less than 40° C., and more preferably not less than 41° C. When another instrument is used for determination, the cloud point may be specified in other terms. An upper limit for the cloud point is not critical and therefore there is no need to specify that.

The HPC is used as a constituent of a separating layer separating the core material comprising omeprazole from the enteric coating layer. The HPC quality defined in the present patent application is desirable in fulfilling the criteria on release rate stability and to be suitable for oral administration forms comprising omeprazole.

DETAILED DESCRIPTION OF THE DRAWINGS

FIG. 1 shows two graphs representing two different dosage forms based on two qualities of HPC named Type A and Type B. The graphs show released omeprazole from the dosage forms after 3 months and 6 months storage at accelerated conditions at 40° C. and 75% relative humidity. The two HPC qualities are used as a constituent of the separating layer described in Example 2 below. With a separating layer comprising HPC Type A the release rate of omeprazole over time has decreased. With the HPC Type B the release rate of omeprazole over time is almost the same as for a freshly produced product.

FIG. 2 shows two graphs representing two different qualities of HPC named Type A and Type B. The graphs show cloud point determinations for the two HPC qualities used as a constituent of the separating layer described in Examples 1–3 below.

FIG. 3a) and FIG. 3b) show graphs representing two different dosage forms based on two qualities of HPC named Type A and Type B. FIG. 3a) shows released omeprazole from dosage forms comprising HPC type A, i.e. a reference. FIG. 3b) shows released omeprazole from dosage forms comprising HPC type B, i.e. according to the invention. The two HPC qualities are used as a constituent of the separating layer described in Example 1 below.

DETAILED DESCRIPTION OF THE INVENTION

Core Materials.

Omeprazole with formula Ia, is preferably formulated into an oral composition in the form of a pharmaceutically acceptable salt, such as an alkaline salt selected from the group of the $Mg^{2+}$, $Ca^{2+}$, $Na^+$ and $K^+$ salts, more preferably the Mg salt. Omeprazole may also be used in the form of one of the single enantiomers of omeprazole or an alkaline salt of one of the single enantiomers of omeprazole, especially an alkaline salt of the (−)-enantiomer of omeprazole, and more preferably the $Mg^{2+}$ salt of the (−)-enantiomer of omeprazole.

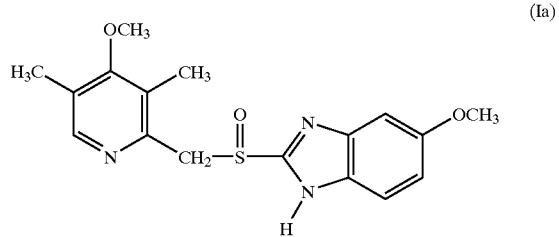

(Ia)

The core material for the individually enteric coating layered pellets can be composed and formulated according to different principles, such as described in EP 247 983 and WO 96/01623 hereby incorporated by reference. For instance, omeprazole is mixed with one or more pharmaceutical constituents to obtain preferred handling and processing properties and also to obtain a suitable concentration of omeprazole in the final mixture. Pharmaceutical constituents such as fillers, binders, lubricants, disintegrating agents, surfactants and other pharmaceutically acceptable additives, can be used.

Preferably, omeprazole, optionally after mixing with an alkaline compound, is mixed with suitable constituents including a binding agent and formulated into a core material. Said core materials may be produced by extrusion/spheronization, balling or compression and by utilizing different process equipment. The formulated core materials may have a size of less than approximately 2 mm. The manufactured core materials can be layered further with additional ingredients, optionally comprising active substance, and/or be used for further processing.

Alternatively, inert seeds layered with active substance (the active substance is optionally mixed with alkaline compounds) can be used as the core material for the further processing. The seeds, which are to be layered with the active substance, can be water insoluble seeds comprising different oxides, celluloses, organic polymers and other materials, alone or in mixtures or water soluble seeds comprising different inorganic salts, sugars, non-pareils and other materials, alone or in mixtures.

Before the seeds are layered, for instance by using granulating or spray coating/layering equipment, omeprazole is mixed with a binding agent and optionally further components. Such further components can be binders, surfactants, fillers, disintegrating agents, alkaline additives or other pharmaceutically acceptable ingredients, alone or in mixtures.

The binders are for example celluloses such as hydroxypropyl methylcellulose, hydroxypropyl cellulose, microcrystalline cellulose and carboxymethyl-cellulose sodium, polyvinyl pyrrolidone, sugars, starches and other pharmaceutically acceptable substances with cohesive properties. Suitable surfactants are found in the groups of pharmaceutically acceptable non-ionic or ionic surfactants, such as for instance sodium lauryl sulphate.

The active substance may also be mixed with an alkaline pharmaceutically acceptable substance (or substances). Such substances can be chosen among, but are not restricted to, substances such as the sodium, potassium, calcium, magnesium and aluminium salts of phosphoric acid, carbonic acid, citric acid or other suitable weak inorganic or organic acids; aluminium hydroxide/sodium bicarbonate co-precipitate; substances normally used in antacid preparations such as aluminium, calcium and magnesium hydroxides; magnesium oxide or composite substances, such as $Al_2O_3 \cdot 6MgO \cdot CO_2 \cdot 12H_2O$, $Mg_6Al_2(OH)_{16}CO_3 \cdot 4H_2O$, MgO.Al$_2$O$_3$. 2SiO$_2$.nH$_2$O or similar compounds; organic ph-buffering substances such as trihydroxy methyl amino methane, basic amino acids and their salts or other similar, pharmaceutically acceptable pH-buffering substances.

Alternatively, the aforementioned core material can be prepared by using spray drying or spray congealing technique.

Separating Layer(s)

The core material containing omeprazole must, according to EP 247 983, be separated from the enteric coating polymer(s) containing free carboxyl groups, which may otherwise cause degradation/discolouration of omeprazole during the coating process or during storage.

According to the present invention, the separating layer comprises a specific quality of HPC. This specific quality of HPC should preferably have a cloud point of at least 38° C. determined by a Mettler instrument. The cloud point is determined in a mixed disodium hydrogenphosphate buffer 0.086 M and hydrochloric acid 0.1 M in the proportions 7:3. The mixed solution used for the cloud point determination has a pH of 6.75–6.85. The concentration of HPC in the mixed solution is 1.0% (w/w) for the Mettler instrument. For more detailed information on the composition of the mixed solution, see below in the experimental section. Preferably, the HPC has a low viscosity, such as for instance below 400 mpas in a 5% (w/w) water solution at 25° C.

Alternatively, the quality of HPC may be determined by a method that correlates with the method described above, e.g. NIR spectrophotometry.

Additives such as plasticizers, colorants, pigments, fillers, anti-tacking, buffering agents, and anti-static agents, such as for instance magnesium stearate, titanium dioxide, talc, and other additives may also be included in the separating layer(s).

Enteric Coating Layer(s)

One or more enteric coating layers are applied onto the core material covered with separating layer(s) by using a suitable coating technique. The enteric coating layer material may be dispersed or dissolved in either water or in a suitable organic solvent. As enteric coating layer polymers one or more, separately or in combination, of the following polymers can be used; e.g. solutions or dispersions of methacrylic acid copolymers, cellulose acetate phthalate, cellulose acetate butyrate, hydroxypropyl methylcellulose phthalate, hydroxypropyl methylcellulose acetate succinate, polyvinyl acetate phthalate, cellulose acetate trimellitate, carboxymethylethylcellulose, shellac or other suitable enteric coating layer polymer(s). For environmental reasons, an aqueous coating process may be preferred. In such aqueous processes methacrylic acid copolymers are most preferred.

The enteric coating layers may contain pharmaceutically acceptable plasticizers to obtain desirable mechanical properties, such as flexibility and hardness of the enteric coating layers. Such plasticizers are for instance, but not restricted to, triacetin, citric acid esters, phthalic acid esters, dibutyl sebacate, cetyl alcohol, polyethylene glycols, polysorbates or other plasticizers. The amount of plasticizer is optimized for each enteric coating layer formula, in relation to selected enteric coating layer polymer(s), selected plasticizer(s) and the applied amount of said polymer(s). Additives such as dispersants, colorants, pigments, polymers e.g. poly(ethylacrylate, methylmethacrylate), anti-tacking and anti-foaming agents may also be included in the enteric coating layer(s). Other compounds may be added to increase film thickness and to decrease diffusion of acidic gastric juices into the acidic susceptible active substance.

To protect the acidic susceptible active substance, the enteric coating layer(s) preferably constitute(s) a thickness of at least approximately 10 µm. The maximum thickness of the applied enteric coating layer(s) is normally only limited by processing conditions.

The pellets or units covered with enteric coating layer(s) may further be covered with one or more over-coating layer(s). The over-coating layer(s) can be applied to the enteric coating layered pellets by coating or layering procedures in suitable equipment such as coating pan, coating granulator or in a fluidized bed apparatus using water and/or organic solvents for the layering process.

Final Dosage Form.

The prepared pellets may be filled in hard gelatine capsules or compressed with suitable tablet excipients into a tableted multiple unit formulation, and the latter is preferred. Final dosage forms may also include but is not restricted to effervescent tablets, and combinations of omeprazole with other active ingredients, such as for instance antibacterial substances, NSAID(s), motility stimulating agents or antacids.

Experimental Section.

EXAMPLE 1

Test of Omeprazole Multiple Unit Tablets, in which the Pellets are Layered with Different Types of HPC Used as a Constituent of the Separation Layer (Laboratory Scale).

Omeprazole tablets with the following composition were prepared according to the description in WO 96/01623. Sugar spheres were spray layered in a fluidized bed with an aqueous suspension of omeprazole magnesium salt and HPMC. The prepared pellets were layered with a separating layer and thereafter enteric coated. Enteric coated pellets were mixed with tablets excipients and compressed into a multiple unit tablet.

The composition of the tested omeprazole tablets (20 mg strenght) was as follows.

| NAME OF INGREDIENT | FORMULA (mg/tablet) |
|---|---|
| Omeprazole magnesium | 20.6 |
| Glyceryl monostearate | 1.4 |
| Hydroxypropylcellulose | 4.8 |
| Hydroxypropyl metylcellulose | 4.6 |
| Magnesium stearate | 0.7 |
| Methacrylic acid copolymer type C | 27 |
| Microcrystalline cellulose | 220 |
| Polysorbate 89 | 0.1 |
| Polyvinylpyrrolidone crosslinked | 4.6 |
| Sodium stearyl fumarate | 0.5 |
| Sugar spheres | 22 |
| Talc | 8.3 |
| Triethyl citrate | 8.2 |

Omeprazole multiple unit tablets prepared with a separating layer on the pellets which separating layer comprises HPC, of either quality i.e type A or type B. HPC of the two types fulfill all requirements in the PhEur as well as the USP. However, the HPC of the two types differ with respect to some physical/chemical characteristics, e.g. cloud point.

The prepared tablets were tested according to the description below. The tablets, i.e. the pellets, were prepared from the same batch of omeprazole magnesium, and with the same enteric coating material. The release of omeprazole was tested on stored tablets after 0 month, and 6 months storage. The amount of released omeprazole within 30 minutes in a buffer solution was determined.

The tablets were pre-exposed to hydrochloric acid at 37° C. for 2 hours. Thereafter the drug release in buffer solution pH 6.8 at 30 minutes was determined by liquid chromatography. The buffer solution pH 6.8 was a mixture of disodium hydrogenphosphate buffer 0.086 M and hydrochloric acid 0.1 M in the proportions 7:3, pH should be between 6.75 and 6.85. The hydrochloric acid 0.1 M was prepared by dissolving 213 ml of conc. HCl in water and added with water to 25 000 ml. The disodium hydrogen phosphate solution 0.086 M was prepared by dissolving 382 g $Na_2HPO_4.2H_2O$ in water and dilute to 25 000 ml with water.

The stability testing was performed on (20 mg strength) tablets packed in plastic bottles with desiccant (the tablets were not covered by a tablet coat).

Results are shown in FIG. 3a) and FIG. 3b). FIG. 3a) shows results with the HPC quality type A, i.e. a reference, and FIG. 3b) shows results with HPC type B, i.e. according to the instant invention.

EXAMPLE 2

Release of Omeprazole from Tablets Comprising Different Types of HPC as a Constituent of the Separating Layer Pilot scale batches (using HPC of type A: 6 batches, and type B: 2 batches) were manufactured in order to confirm the improvement found during the laboratory testing in Example 1. Results from stability studies are shown in FIG. 1.

The comparison clearly indicates improved release rate stability for tablets containing HPC of type B relative to that of type A.

General compositions for omeprazole tablets (20 mg strength):

| NAME OF INGREDIENT | FORMULA (mg/tablet) |
|---|---|
| Omeprazole magnesium | 20.6 |
| Colour iron oxide reddish-brown | 0.3 |
| Glyceryl monostearate | 1.4 |
| Hydroxypropylcellulose | 4.8 |
| Hydroxypropyl metylcellulose | 15 |
| Magnesium stearate | 0.7 |
| Methacrylic acid copolymer type C | 27 |
| Microcrystalline cellulose | 220 |
| Paraffin | 0.2 |
| Polyethylene glycol 6000 | 2.5 |
| Polysorbate 80 | 0.1 |
| Polyvinylpyrrolidone crosslinked | 4.6 |
| Sodium stearyl fumarate | 0.5 |
| Sugar spheres | 22 |
| Talc | 8.3 |
| Titanium dioxide | 2.2 |
| Triethyl citrate | 8.2 |

The tablets were manufactured as described in example 1, with the additional step of a tablet coat comprising HPMC, PEG 6 000, and pigment.

EXAMPLE 3

Cloud Point Determinations

Omeprazole tablets were manufactured in laboratory scale as described in example 1.

Cloud point determinations of the HPC types in the Mettler instrument was conducted in the following way. The cloud point of the HPC types was determined in a mixed phosphate buffer 0.086 M and hydrochloric acid 0.1 M in the proportions 7:3. The mixed solution used for the cloud point determination had a pH of 6.75–6.85. The concentration of HPC in the mixed solution was 1.0% (w/w). It is essential for the specificity of the cloud point determination that this system is used in the chosen instrument. The Mettler instrument comprises the following parts: Mettler FP90 Central processor, FP81C Measuring unit and ME-18572 boiling point tubes. A temperature range of 30.0 to 50.0° C. was used and a heating rate of 1.0° C./min. The cloud point is defined as the temperature where the light transmission is 96%.

The results are shown in FIG. 2.

What is claimed is:

1. An enteric coated oral pharmaceutical formulation comprising:

(a) a core material which comprises an active ingredient selected from the group consisting of omeprazole, an alkaline salt of omeprazole, one of the single enantiomers of omeprazole and an alkaline salt of one of the single enantiomers of omeprazole;

(b) a separating layer; and (c) an enteric coating layer, wherein the separating layer comprises a hydroxypropyl cellulose (HPC) with a cloud point of at least 38° C., and wherein the light transmission at cloud point of a system comprising the HPC dissolved in a concentration of 1.0% (w/w) in a mixed solution of disodium hydrogen phosphate buffer 0.086 M and hydrochloric acid 0.1 M in the proportions 7:3 at a pH of 6.75–6.85 is 96%.

2. The formulation according to claim 1, wherein the HPC has a cloud point of at least 40° C.

3. The formulation according to clam 1, wherein the HPC has a cloud point of at least 41° C.

4. The formulation according to claim 1, wherein the enteric coating layer comprises a methacrylic acid copolymer.

5. The formulation according to claim 1, wherein the HPC has a low viscosity.

6. The formulation according to claim 1, wherein the active ingredient is omeprazole.

7. The formulation according to claim 1, wherein the active ingredient is a magnesium salt of omeprazole.

8. The formulation according to claim 1, wherein the active ingredient is a magnesium salt of the (−)-enantiomer of omeprazole.

9. The formulation according to claim 1, wherein the core material further comprises an alkaline reacting compound.

10. The formulation according to claim 1 or 9, wherein the core material further comprises a pharmaceutically acceptable excipient selected from the group consisting of binding agents, fillers, lubricants, disintegrating agents, surfactants and mixtures thereof.

11. A method for the treatment of gastrointestinal diseases in mammals comprising administering to a host in need thereof a therapeutically effective amount of the pharmaceutical formulation according to any one of claims 2–8 or 1.

12. A process for the manufacture of an enteric coated oral pharmaceutical formulation according to claim 1, comprising the steps:

(a) forming the core material comprising the active ingredient;

(b) applying the separating layer onto the core; and (c) applying the enteric coating layer onto the core coated with the separating layer.

13. The process according to claim 12, wherein an alkaline reacting compound is mixed with the active ingredient to form the core material.

14. The process according to claim 12 or 13, wherein a pharmaceutically acceptable excipient selected from the group consisting of binding agents, fillers, lubricants, disintegrating agents, surfactants and mixtures thereof is added to form the core material.

15. The process according to claim 12, wherein an alkaline reacting compound is mixed with the active ingredient and a binding agent to form the core material.

16. The process according to claim 12, wherein the HPC has a cloud point of at least 40° C.

17. The process according to claim 12, wherein the HPC has a cloud point of at least 41° C.

18. The process according to claim 12, wherein the enteric coating layer comprises a methacrylic acid copolymer.

19. The process according to claim 12, wherein the HPC has a low viscosity.

20. The process according to claim 12, wherein the active ingredient is omeprazole.

21. The process according to claim 12, wherein the active ingredient is a magnesium salt of omeprazole.

22. The process according to claim 12, wherein the active ingredient is a magnesium salt of the (−)-enantiomer of omeprazole.

* * * * *